United States Patent [19]

Fluke

[11] Patent Number: 5,304,137
[45] Date of Patent: Apr. 19, 1994

[54] SAFETY SYRINGE

[76] Inventor: Gary L. Fluke, 16824 Broadway, Snohomish, Wash. 98290

[21] Appl. No.: 59,325

[22] Filed: May 7, 1993

[51] Int. Cl.$^5$ .............................................. A61M 5/00
[52] U.S. Cl. ................................... 604/110; 604/198
[58] Field of Search ............... 604/198, 263, 110, 187, 604/192, 195

[56] References Cited

U.S. PATENT DOCUMENTS

| | | | |
|---|---|---|---|
| 4,943,281 | 7/1990 | Kothe | 604/263 X |
| 4,994,042 | 2/1991 | Vadher | 604/198 X |
| 5,201,708 | 4/1993 | Martin | 604/110 |
| 5,201,720 | 4/1993 | Borgia et al. | 604/198 |

Primary Examiner—John D. Yasko
Attorney, Agent, or Firm—Dean A. Craine

[57] ABSTRACT

A safety hypodermic syringe designed to prevent accidental puncture injuries including a syringe body with a needle assembly having a protective sleeve member which slides over the needle and protects the user from accidental punctures. The syringe is designed so that the sleeve member automatically covers the needle when the syringe is not in use. Disposed between the end of the syringe body and the sleeve member is a biasing means, such as a spring, which forcibly moves the sleeve member downward over the needle covering the distal end thereof. Disposed on opposite sides of the syringe body parallel to the longitudinal axis thereof are two flexible arms which when pressed inward, allow the sleeve member to slide upward so that the user may insert the end of the needle into the skin. When the needle is removed from the skin, the spring forces the sleeve member downward over the end of the needle.

13 Claims, 3 Drawing Sheets

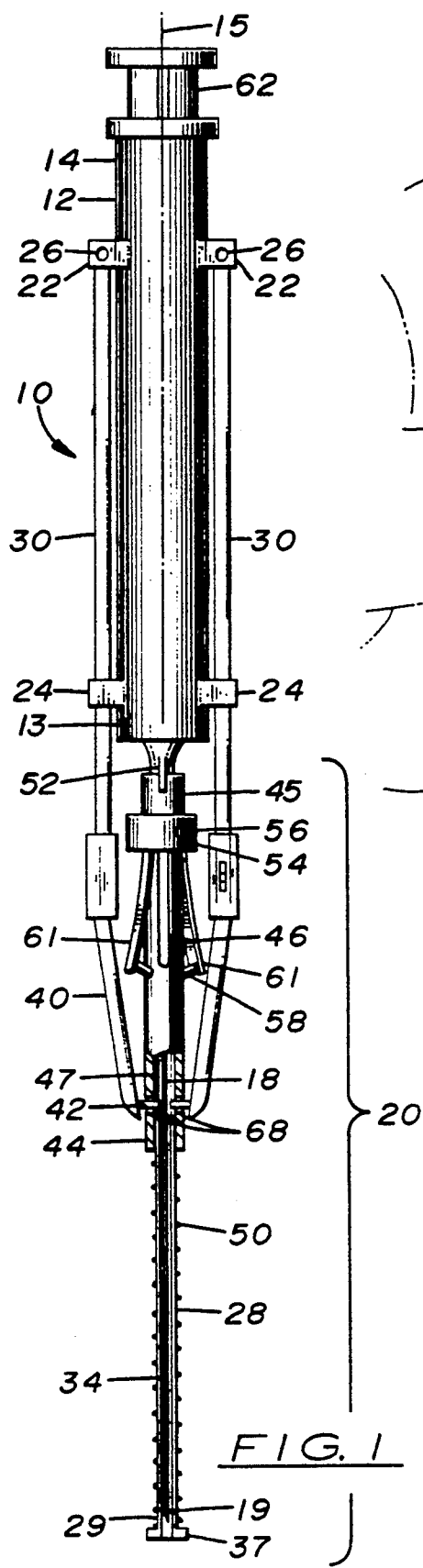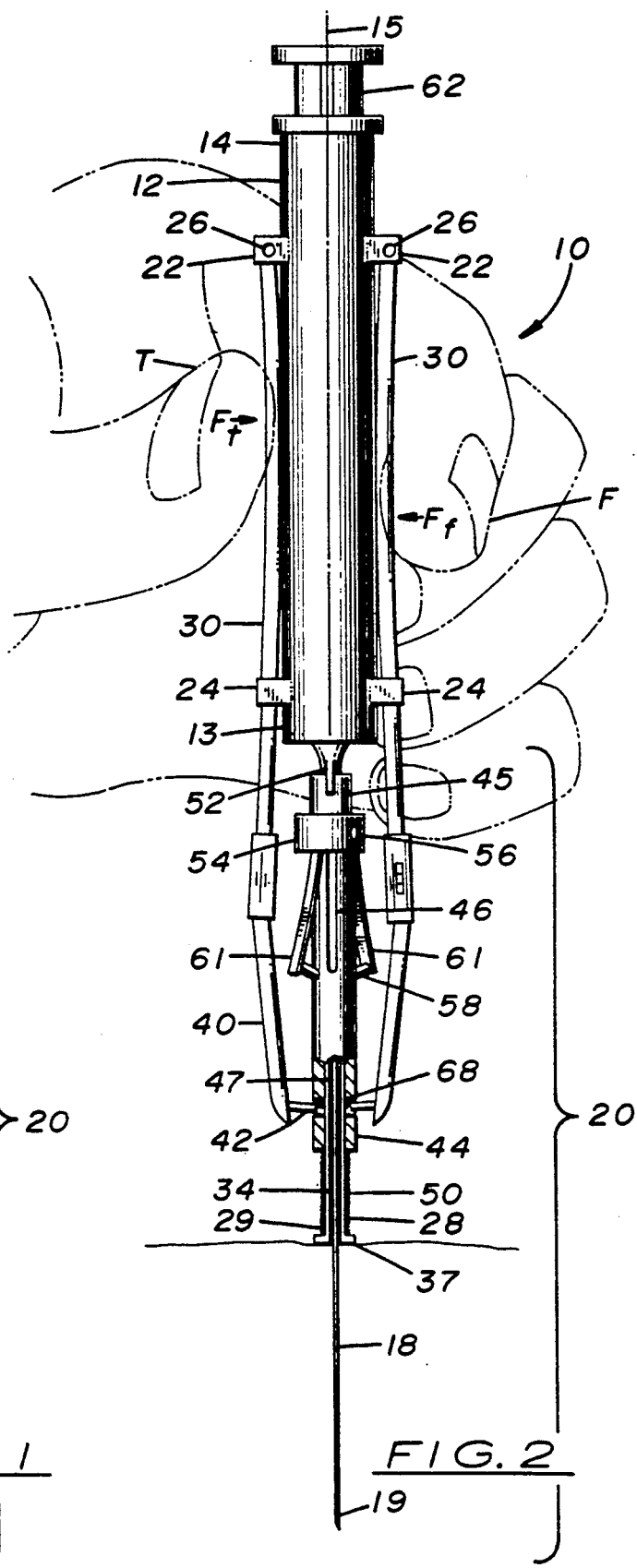

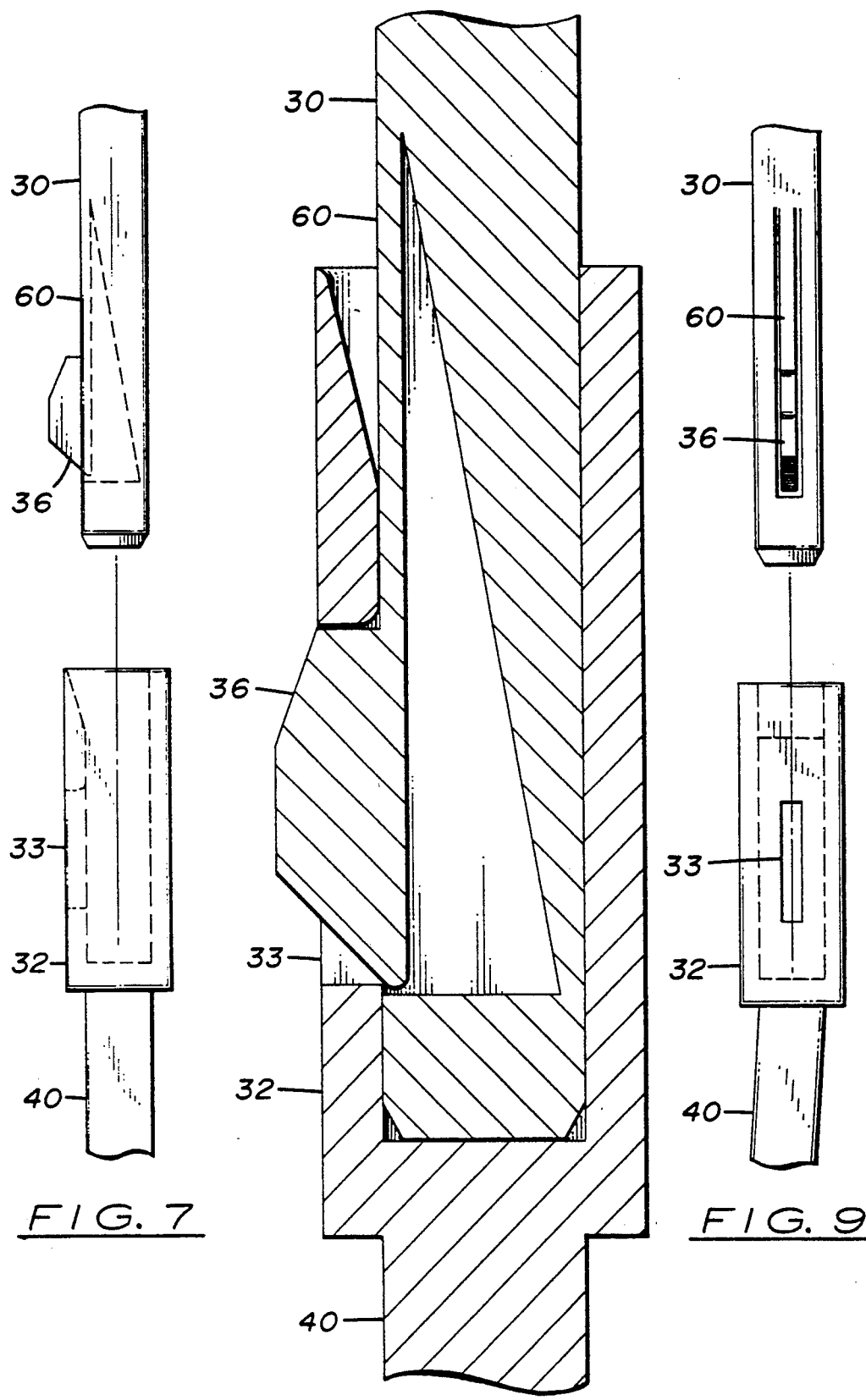

SAFETY SYRINGE

BACKGROUND OF THE INVENTION

1. Field of the Invention:

This invention relates to hypodermic syringes and, more particularly, to hypodermic syringes designed to prevent accidental punctures.

2. Description of the Related Art:

Blood borne disease transmission has reached epidemic proportion. Medical personnel and patients need protection from accidental needle puncture wounds, as even the slightest injury caused by contact with a contaminated needle may be lethal. Of exceptional concern is the spread of the Acquired Immune Deficiency Syndrome (AIDS). In order for a syringe safety device to be effective, and to be accepted by medical industry personnel, it must simultaneously provide the attributes of complete protection, ease and practicality of use, interchangeable needle capability, and reasonable manufacturing cost.

Previously designed needle wound protection devices have failed to provide all of the aforementioned attributes. Many prior art designs do not provide protection from accidental needle contact through all phases of use. The syringe apparatuses set forth in U.S. Pat. No. 4,932,947 and U.S. Pat. No. 4,929,237 are cumbersome and awkward to use. Safety syringes featuring a needle which is automatically withdrawn when the plunger is driven full stroke do not allow for mixing of medicines, nor do they provide protection from accidental puncture through all phases of use. All other prior art safety syringes' protection mechanisms require use of two hands. Various prior art syringe safety devices do not allow for changing of a hypodermic needle. Medical personnel must be free to safely use hypodermic needles of various lengths and diameters.

SUMMARY OF THE INVENTION

It is a general object of the present invention to provide a safety syringe designed to prevent accidental puncture injuries.

It is an object of the present invention to provide such a syringe which operates to automatically covers the needle to prevent injuries.

It is another object of the present invention to provide such a syringe which may be held and operated using one hand.

It is a further object of the present invention to provide such a syringe which is easy to use and economical to manufacture.

These and other objects of the invention are met by providing an improved safety syringe designed to prevent accidental punctures during non-use. The safety syringe comprises a standard cylindrical-shaped syringe body with a needle coupled to the distal or closed end thereof. A sleeve assembly, which includes an upper, fixed receiver and a lower, sleeve member, is disposed longitudinally over the needle. When at rest, a biasing means disposed between the receiver and the sleeve member causes the receiver and sleeve member to separate into an extended position, hereinafter called a first position, over the needle. While in the first position, the distal or exposed end of the needle is covered by the sleeve member to prevent accidental punctures.

Disposed between the syringe body and the sleeve assembly is a finger activated release means which, when selectively activated, allows the user to use the syringe to give an injection. To give an injection, the syringe is held substantially perpendicular to the skin so that the distal end of the sleeve member is pressed against the skin. When the finger activated release means is activated, the user is able to force the syringe body downward to inject the exposed end of the needle into the skin. More specifically, the finger activated release means allows the receiver to slide downward over the sleeve member into a retracted position, hereinafter called a second position. After the fluid inside the syringe body has been injected, the user pulls the syringe body upward. As the syringe body is pulled upward, the biasing means forces the sleeve member and the receiver to separate again into the first position so that the sleeve member again covers the exposed end of the needle.

In the preferred embodiment, the finger activated releasing means is conveniently located on the outside surface of the syringe body so that it may be selectively activated by the user using the same fingers of the hand holding the syringe.

BRIEF DESCRIPTION OF THE DRAWINGS

FIG. 1 is a front elevational view in section of a safety syringe constructed according to the invention;

FIG. 2 shows the syringe of FIG. 1 as the finger activated means is activated with one hand and the needle is penetrating tissue;

FIG. 7 is a partial elevational view of the mating portions of the flexible arm and a stop arm;

FIG. 8 is an enlarged, elevational view of the flexible arm and the stop arm shown in FIG. 7 being joined together, and;

FIG. 9 is a side elevational view of the flexible arm and the stop arm shown in FIG. 7.

DESCRIPTION OF THE PREFERRED EMBODIMENT(S)

Figure 3:
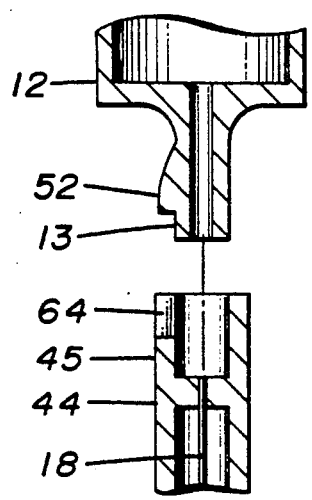
FIG. 3 is a sectional view of a portion of the syringe of FIG. 1 showing the receiver separated from the syringe body.

In the accompanying drawings there is shown a safety syringe, designated 10 designed to meet the above stated objectives.

As shown in FIGS. 1-2, the safety syringe 10 comprises a cylindrical shaped syringe body 12 having a distal end 13, a proximal end 14, and a longitudinal axis 15. Inside the syringe 10 is a plunger 62 capable of being moved longitudinally to push fluids contained therein outward.

Attached to the distal end 13 of the syringe body 12 is an elongated needle cannula, hereinafter known as needle 18, designed for injecting fluids into the human body. Attached over the needle 18 is a sleeve assembly 20 designed to automatically cover the distal end 19 of the needle 18 when not in use. In the preferred embodiment, the sleeve assembly 20 includes a longitudinally aligned cylindrical-shaped receiver 44 and a cylindrical-shaped sleeve member 28. The receiver 44 is fixed at its proximal end to an attachment hub 45 and extends over the upper section of the needle 18. The receiver 44 has a longitudinally aligned central bore 47 which enables the needle 18 to extend therethrough. The needle 18 is also fixed at one end to the attachment hub 45 which is used to couple both the receiver 44 and the needle 18 to the distal end 13 of the syringe body 12.

The sleeve member 28 is positioned over the lower section of the needle 18. The sleeve member 28 is designed to fit inside the central bore 47 of the receiver 44 during use. The sleeve member 28 also has a longitudinally aligned central bore 34 with a sufficient diameter to allow the needle 18 to slide freely therein. The length of the sleeve member 28 is also sufficient so that the distal end 19 of the needle 18 is covered when the sleeve member 28 is in the first position. In the preferred embodiment, a perpendicularly aligned skin platform 37 is manufactured on the distal end 29 of the sleeve member 28. The bottom surface of the platform 37 is sufficiently wide so that sleeve member 28 does not penetrate the patient's skin when the syringe is used to give an injection.

In the preferred embodiment, the sleeve assembly 20 and the needle 18 are designed to be exchangeable with the syringe body 12 so that different size needles 18 may be used. As shown in FIG. 3, the attachment hub 45 on the receiver 44 has a longitudinally aligned slot 64 manufactured therein which engages a laterally projecting prong 52 located on the distal end 13 of the syringe body 12. During assembly, the prong 52 is inserted into slot 64 to align the receiver 44 on the syringe body 12.

As shown in FIGS. 1-2, a biasing means is attached between the sleeve member 28 to forcibly dispose the sleeve member 28 in the first position when the syringe 10 is not in use. In the preferred embodiment, the biasing means comprises a spring member 50 disposed between the sleeve member 28 and the receiver 44. The spring member 50 is placed over the sleeve member 28 with the lower edge thereof fixed to the upper surface of the platform 37. The upper edge of the spring member 50 presses against the distal edge of the receiver 44 to hold the sleeve member 28 in the first position over the needle 18.

A finger activated releasing means is disposed between the syringe body 12 and the sleeve assembly 20. The finger activated releasing means is designed to automatically lock the sleeve member 28 in the first position when the syringe 10 is not in use. When the finger activated releasing means is activated, the receiver 44 is able to freely move downward over the sleeve member 28 pushing the distal end 19 of the needle 18 beyond the distal end 29 of the sleeve member 28.

Figure 4:
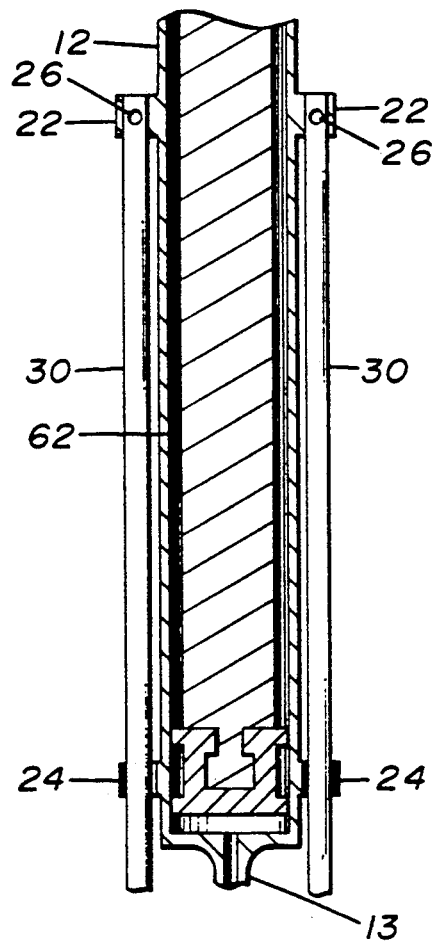
FIG. 4 is an elevational view in section of a portion of the syringe of FIG. 1 depicting the syringe body and the brackets and anchors to which the flexible arms are mounted.
Figure 6:
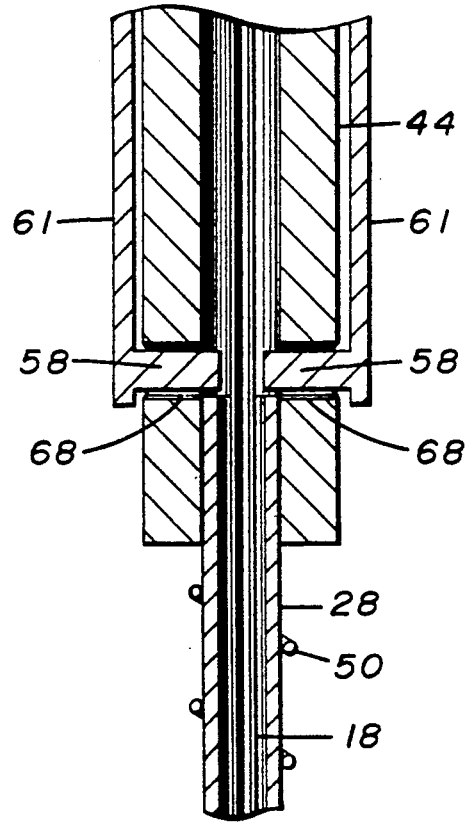
FIG. 6 is a partial elevational view in section of the receiver shown in FIG. 5 with the stop pins in position to interfere with movement of the sleeve member.

In the preferred embodiment, the finger activated releasing means comprises two flexible arms 30, two stop pins, 40, and two stop bores 68. A pair of outward projecting anchors 22 are attached to the outer surface of the syringe body 12 near the opened proximal end 14. A pair of outward projecting brackets 24 are attached to the outer surface of the syringe body 12 near the closed distal end 13. The pair of anchors 22 and brackets 24 are vertically aligned on opposite sides of the syringe body 12. Aligned longitudinally on opposite sides of the syringe body 12 is a pair of flexible arms 30. The flexible arms 30, which are constructed of resilient plastic material, are held and aligned in a parallel position to longitudinal axis 15 of the syringe body 12 by anchors 22 and brackets 24. As shown in FIG. 4, the proximal ends of the flexible arms 30 are fixed to the anchors 22 by pins 26. The brackets 24 loosely retain the flexible arms 30 in position on the syringe body 12 and act as fulcrum points so that the distal ends of the flexible arms 30 may move outward when the central regions thereof are pushed inward by the user.

The distal end of each flexible arm 30 extends beyond the distal end 13 of the syringe body 12 and attaches to the proximal end of a diagonally aligned stop arm 40. In the embodiment shown, an attachment means is disposed between the distal end of each flexible arm 30 and the proximal end of the adjoining stop arm 40 which enables them to be selectively attached and detached. In the preferred embodiment, the attachment means comprises a socket 32 attached to the proximal end of each stop arm 40. As shown in FIGS. 7, 8, and 9, attached to the distal end of each flexible arm 30 is a sear 36 and a leaf spring 60. The flexible arm 30, the sear 36, and the leaf spring 60 are integrally attached and are made of molded, resilient plastic material.

As shown in FIGS. 1-2, during use the syringe body 12 is held by gripping the flexible arms 30 using the thumb (T) and index finger (F) on one hand. Until the flexible arms 30 are forced inward by pinching the thumb (T) and index finger (F) together, the stop pins 42 prevent any longitudinal movement of the sleeve member 28 over the needle 18. When the operator wants to insert the needle 18 into an injection site, the operator holds the syringe body 12 and simultaneously pinches the central region of the flexible arms 30 inward using the thumb (T) and index finger (F). As the forces $F_t$ and $F_f$ are exerted by the thumb (T) and index finger (F), respectively, on the flexible arms 30, the distal ends of the flexible arms 30 move outward from the syringe body 12 which causes the distal ends of the adjoining stop arms 40 to simultaneously move outward. As the distal ends of the stop arms 40 move outward, the stop pins 42 are pulled from the holes 68 to allow the receiver 44 to move downward over the sleeve member 28. Once the proximal end of the sleeve member 28 has passed stop pins 42, the operator need not continue pinching the flexible arms 30.

After the operator has given the injection, the needle 18 is withdrawn from the injection site. As the syringe body 12 is pulled upward, the receiver 44 is pulled upward over the sleeve member 28. The spring member 50 forces the sleeve member 28 downward over the needle 18. Referring to FIG. 1, the sleeve member 28 comes to rest when its proximal end passes holes 68 manufactured in the receiver 44. With the operator gripping safety syringe 10 in a relaxed manner, not purposely pinching flexible arms 30, stop pins 42 reenter holes 68 as flexible arms 30 return to their original shape. Therefore, the sleeve member 28 cannot move to expose the needle 18 unless the operator again pinches flexible arms 30.

Referring to FIG. 8, the flexible arm 30 is aligned with an adjoining stop arm 40 by engaging the sear 36 with a slot 33 located on the socket 32 and leaf spring 60 is in a relaxed state. To disengage the stop arm 40 from the flexible arm 30, the operator grips the socket 32 with his or her thumb and index finger in a way such that one of the digits presses the sear 36 inward. Leaf spring 60 thus flexes and allows the sear 36 to move inward, away from the slot 33. As the operator begins to disengage the stop arm 40 from the flexible arm 30, the sear 36 slides against the proximal end of the slot 33, causing the sear 36 to move further inward until it no longer resides in the slot 33. Stop arm 40 and the flexible arm 30 can then be disengaged. When both pairs of stop arms 40 and flexible arms 30 are disengaged, the sleeve assembly 20 may be removed from the syringe body.

Figure 5:
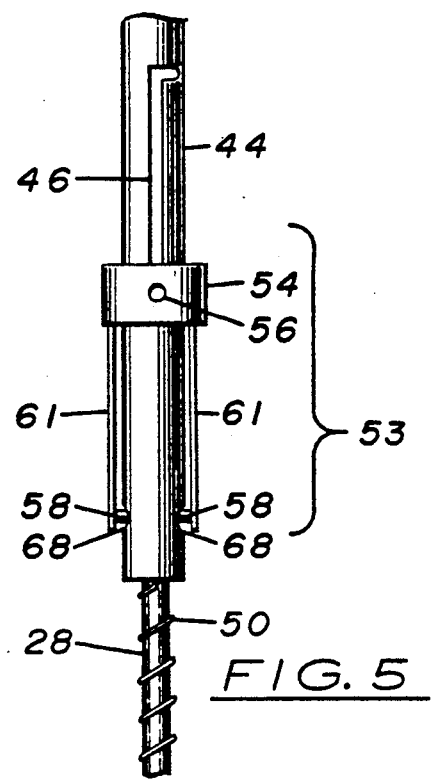
FIG. 5 is a partial elevational view of the detached receiver illustrating the stop pins in an engaged position allowing for coverage of the needle throughout the disposal process.

Referring to FIG. 5, fitted to the receiver 44 is an optional sheath lock 53 which enables the user to lock the needle 18 and the sleeve assembly 20 in first position for safe transport. The sheath lock 53 comprises a collar 54, a guide pin 56, leaf springs 61 and second stop pins 58. Guide pin 56 resides in a flute 46. The sheath lock 53 is engaged by first rotating the collar 54 about the axis of the receiver 44 until the guide pin 56 aligns with the longitudinal portion of the flute 46. The collar 54 is slid distally along the receiver 44 until stop pins 58 are forced into the holes 68 by leaf springs 61. Sleeve member 28 cannot then move proximally to expose needle 18. As shown in FIG. 3, receiver 44 may then be removed and disposed of to allow the fitting of a receiver with a differently sized needle to syringe body 12. To continue using the safety syringe 10, the stop arms 40 are positively engaged with the flexible arms 30 by simply inserting fully the distal ends of the flexible arms 30 into the sockets 32, as shown in FIG. 8. The compliance of the leaf springs 61 allows the sears 36 to be automatically displaced as the stop arms 40 are re-engaged.

In compliance with the statute, the invention has been described in language more or less specific as to structural features. It should be understood, however, that the invention is not limited to the specific features shown since the means and construction shown comprises the preferred forms of putting the invention into effect. The invention is, therefore, claimed in any of its forms or modifications within the legitimate and valid scope of the amended claims, appropriately interpreted in accordance with the doctrine of equivalents.

I claim:

1. A safety syringe, comprising:
   a. a syringe body having a distal end, a proximal end, and a longitudinal axis, said syringe body also including a plunger capable of pushing fluid contained inside said syringe body through said distal end;
   b. a needle coupled to said distal end of said syringe body, said needle having an exposed distal end capable of being inserted into the skin;
   c. a sleeve assembly attached to said syringe body and disposed longitudinally over said needle, said sleeve assembly includes a longitudinally aligned, slidingly connected receiver and sleeve member, said receiver being fixed at one end to said distal end of said syringe body, said sleeve member having a distal end, said sleeve member capable of being slidingly disposed into a first position over said needle so that said distal end of said needle is covered by said sleeve member, said sleeve member also capable of being slidingly disposed into a second position over said needle so that said distal end of said needle is exposed;
   d. A biasing means attached to said sleeve assembly which forcibly disposed said sleeve member in said first position over said needle when said syringe is not in use, and;
   e. finger activated releasing means disposed between said syringe body and said sleeve assembly, said finger activated releasing means capable of automatically locking said sleeve member in said first position over said needle when said syringe is not in use, said finger activated releasing means also capable of being activated by said user to enable said sleeve member to be slidingly disposed in said second position over said needle by pressing said distal end of said sleeve member against said skin and forcing said syringe body toward said skin to insert said distal end of said needle therein.

2. A safety syringe, as recited in claim 1, wherein said biasing means includes a spring member disposed between said sleeve member and said receiver.

3. A safety syringe, as recited in claim 2, further including said sleeve member having a platform located on said distal end of said sleeve member which enables said sleeve member to be pressed adjacent to said skin when said syringe is used to give an injection.

4. A safety syringe, as recited in claim 2, wherein said finger activated releasing means includes two flexible arms, disposed in a suspended position on opposites side of said syringe body parallel to said longitudinal axis thereof, each said flexible arm having an extending end with a stop pin attached thereto, said finger activated releasing means further including a pair of stop pin bores formed in said sleeve assembly and aligned with said stop pins, said flexible arms being attached and aligned on said syringe body and said stop pin bores being aligned on receiver so that when said stop pins are engaged in said stop pin bores, longitudinal movement of said receiver and said sleeve member is prevented, said flexible arms being attached to said syringe body so that when the central region of said flexible arms are pressed inward, the extending ends of said flexible arms move outward to disengage said stop pins from said stop pin bores, thereby enabling said receiver to slide downward over said sleeve member.

5. A safety syringe, as recited in claim 4, further including each said flexible arm having a coupling means enabling each said flexible arm to be disassembled from said syringe body.

6. A safety syringe, comprising:
   a. a syringe body having a distal end, a proximal end, and a longitudinal axis, said syringe body also including a plunger capable of pushing fluid contained inside said syringe body through said distal end;
   b. a needle coupled to said distal end of said syringe body, said needle having an exposed end capable of being injected into the skin;
   c. a sleeve assembly slidingly attached over said needle, said sleeve assembly capable of being selectively disposed in a first position sot that said distal end of said needle is covered and in a second position so that said exposed end of said needle is exposed;
   d. a spring attached to said sleeve assembly capable of disposing said sleeve assembly in a first position over said needle when said syringe is not in use, and;
   e. a finger activated releasing means including two flexible arms, two stop pins, and two stop pin bores, said flexible arms being disposed in a suspended position on opposite sides of said syringe body parallel to said longitudinal axis thereof, each said flexible arm having a pivot means, said pivot means enabling said movable end to be forcibly moved outward in a direction perpendicular to said longitudinal axis when said central region of said flexible arm is pressed inward, each said flexible arm having one stop pin aligned and attached to said moveable end, each said stop pin being aligned substantially perpendicular to said longitudinal axis of said syringe body and, said stop pin bores being aligned on said receiver so that when said stop pins are engaged therewith, sliding movement of said receiver over said sleeve member is prevented.

7. A safety syringe, as recited in claim 6, further including said sleeve member having a platform located on said distal end of said sleeve member which enables said sleeve member to be comfortably pressed against said skin during use.

8. A safety syringe, as recited in claim 7, further including each said flexible arm having a coupling means enabling each said flexible arm to be disassembled from said syringe body.

9. A safety syringe, comprising:
a. a syringe body having a distal end, a proximal end, and a longitudinal axis, said syringe body also including a plunger capable of pushing fluid contained inside said syringe body through said distal end;
b. an elongated needle, said needle having an upper section and a lower section, said needle having an upper end capable of being attached to said distal end of said syringe body and an exposed end capable of penetrating the skin;
c. a receiver fixedly attached over said upper section of said needle, said receiver having an elongated central passageway aligned parallel to the longitudinal axis of said needle;
d. a sleeve member sliding supported over said needle, and capable of sliding longitudinally inside said central passageway, said sleeve member having a distal end;
e. a biasing means disposed between said receiver and said sleeve member, said biasing means capable of forcibly disposing said sleeve member in an extended position so that said distal end of said needle is covered when not in use;
f. a finger activated releasing means disposed between said syringe body and said receiver, said finger activated releasing means capable of automatically locking said receiver in said first position when not in use, said finger activated releasing means also capable of being engaged by said user to enable said receiver to be disposed in said second position over said needle, said finger activated releasing means including two flexible arms, disposed in a suspended position on opposite sides of said syringe body parallel to said longitudinal axis thereof, each said flexible arm having an extending end with a stop pin attached thereto, said finger activated releasing means further including a pair of stop pin bores formed in said sleeve assembly and aligned with said stop pins, said flexible arms being attached and aligned on said syringe body and said stop pin bores being aligned on receiver so that when said stop pins are engaged in said stop pin bores, longitudinal movement of said receiver and said sleeve member is prevented, said flexible arms being attached to said syringe body so that when the central region of said flexible arms are pressed inward, the extending ends of said flexible arms move outward to disengage said stop pins from said stop pin bores, thereby enabling said receiver to slide over said sleeve member.

10. A safety syringe, as recited in claim 9, further including said sleeve member having a platform located on said distal end of said sleeve member which enables said sleeve member to be comfortably pressed against said skin during use.

11. A safety syringe, as recited in claim 10, wherein said biasing means includes a spring member disposed between said sleeve member and said receiver.

12. A safety syringe, as recited in claim 11, further including a sheath lock capable of locking said needle and said sleeve member in a first position when disengaged from said syringe.

13. A safety syringe, as recited in claim 12, wherein said sheath lock comprises a collar, a guide pin, and leaf springs.

* * * * *